United States Patent
DeSatnick et al.

[11] Patent Number: 5,916,216
[45] Date of Patent: Jun. 29, 1999

[54] GRAFT FIXATION DEVICES

[75] Inventors: Allen H. DeSatnick, Marblehead; Herbert Marcus, Chelmsford, both of Mass.

[73] Assignee: Wright Medical Technology, Inc., Arlington, Tenn.

[21] Appl. No.: 08/740,849

[22] Filed: Nov. 4, 1996

Related U.S. Application Data

[63] Continuation-in-part of application No. 08/482,472, Jun. 7, 1995, Pat. No. 5,571,184.

[51] Int. Cl.$^6$ .......................... A61B 17/56; A61B 17/58; A61F 2/30
[52] U.S. Cl. ................................ 606/72; 623/13; 606/86; 606/96
[58] Field of Search .................................. 606/60, 72, 86, 606/96, 99; 623/13

[56] References Cited

U.S. PATENT DOCUMENTS

| | | | |
|---|---|---|---|
| 4,537,185 | 8/1985 | Stednitz . | |
| 4,828,562 | 5/1989 | Kenna | 606/72 |
| 4,870,957 | 10/1989 | Goble et al. | 606/73 |
| 4,877,020 | 10/1989 | Vich | 606/86 |
| 4,950,271 | 8/1990 | Lewis et al. | 606/102 |
| 5,067,956 | 11/1991 | Buford, III et al. | 606/73 |
| 5,356,413 | 10/1994 | Martins et al. | 606/75 |
| 5,356,435 | 10/1994 | Thein | 623/15 |
| 5,425,767 | 6/1995 | Steininger et al. | 623/13 |
| 5,571,184 | 11/1996 | DeSatnick | 623/13 |
| 5,632,748 | 5/1997 | Beck, Jr. et al. | 606/72 |

FOREIGN PATENT DOCUMENTS 3630390  3/1987  Germany ................... 606/72

Primary Examiner—Paul B. Prebilic
Attorney, Agent, or Firm—Lappin & Kusmer LLP

[57] ABSTRACT

A graft fixation device for positioning and anchoring a bone graft within a bony channel. The fixation device generally comprises a rigid cylindrical member extending about a central axis, the member including an eccentric bore extending about an axis which is substantially parallel to, and radially offset from, the central axis. The fixation device is adapted to receive a rotational force applied to it. Rotation of the fixation device causes a bone plug installed and secured therein to move laterally within a bony channel, thus bringing the bone plug in contact with a portion of the channel wall. Preferably, the cancellous bone regions of the bone plugs and the bony channel are brought into abutting contact for optimum bone ingrowth opportunity and maximum graft fixation strength.

1 Claim, 8 Drawing Sheets

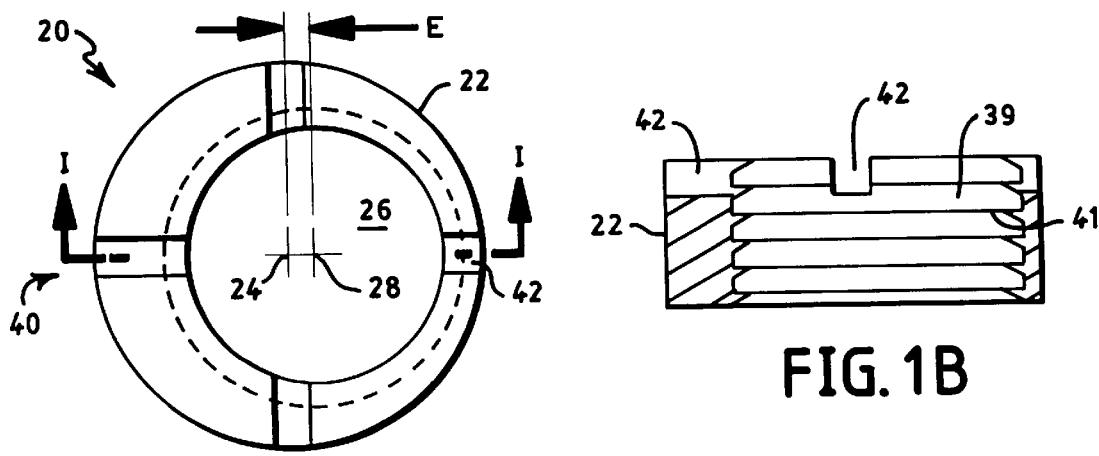
FIG. 1A
FIG. 1B
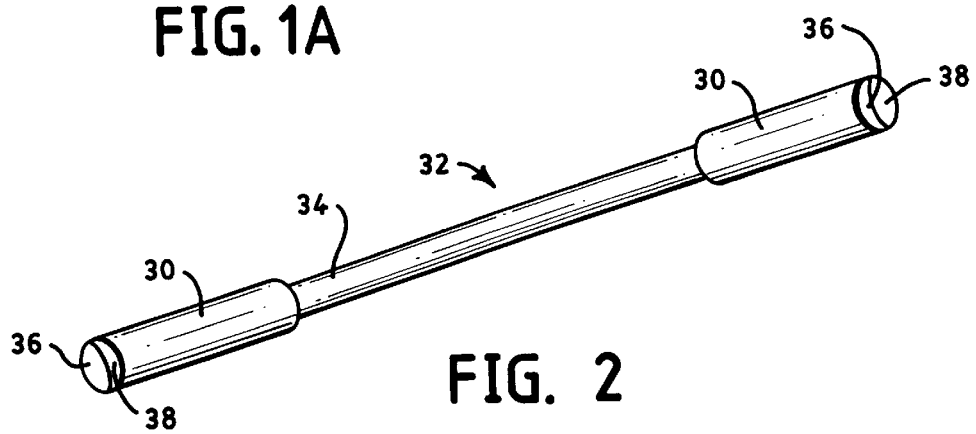
FIG. 2
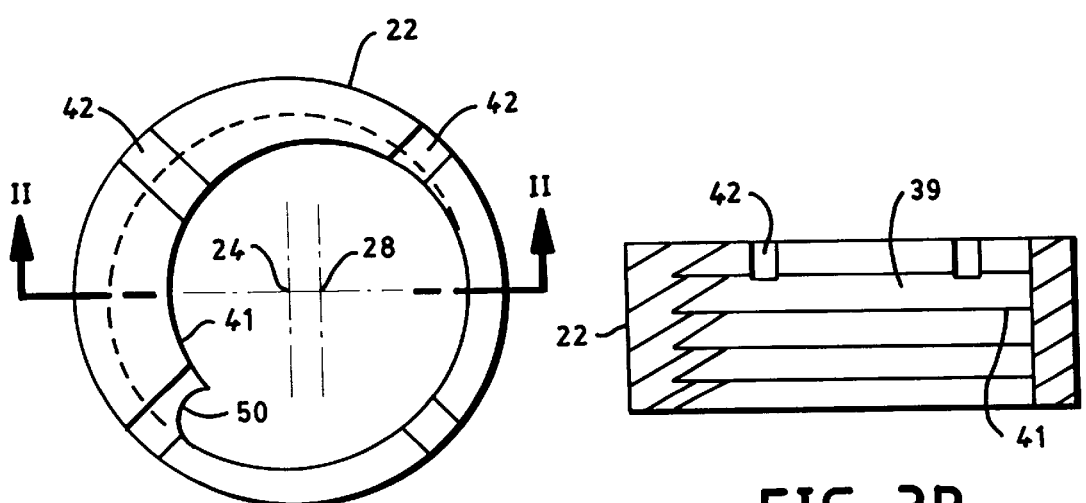
FIG. 3A
FIG. 3B

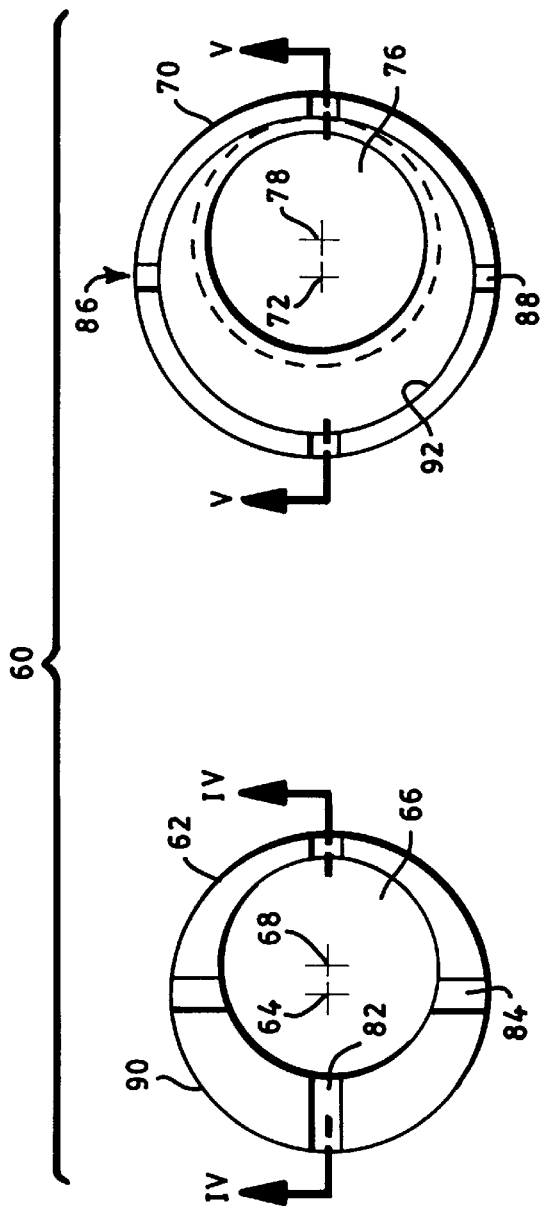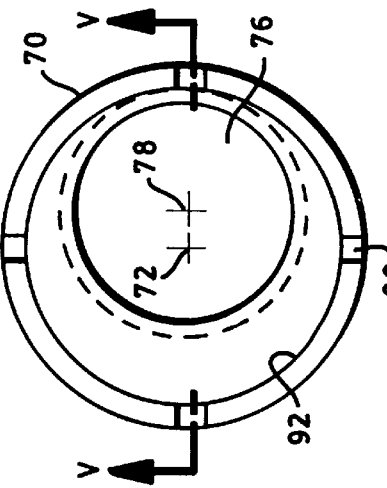

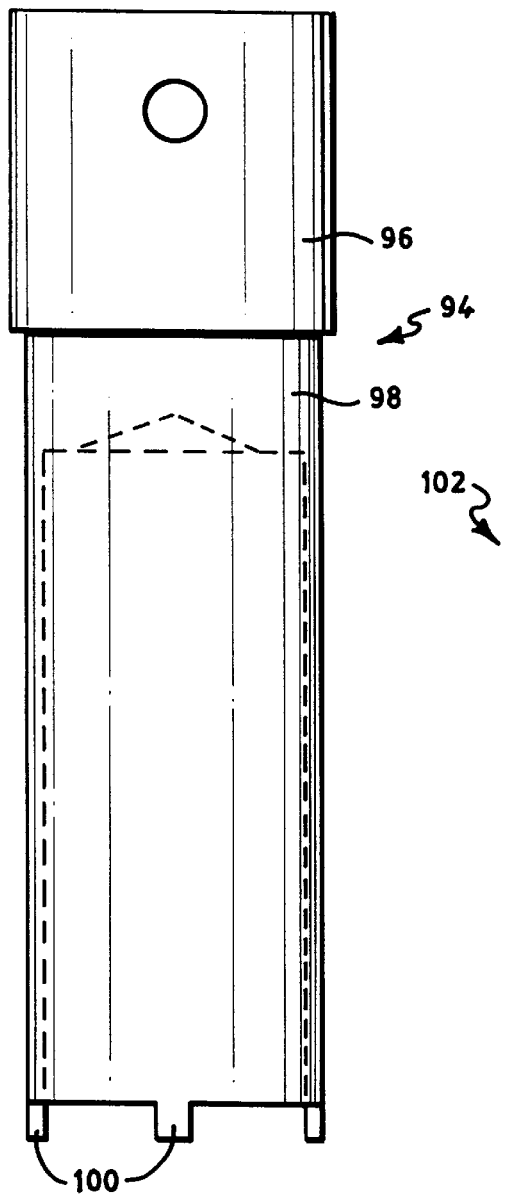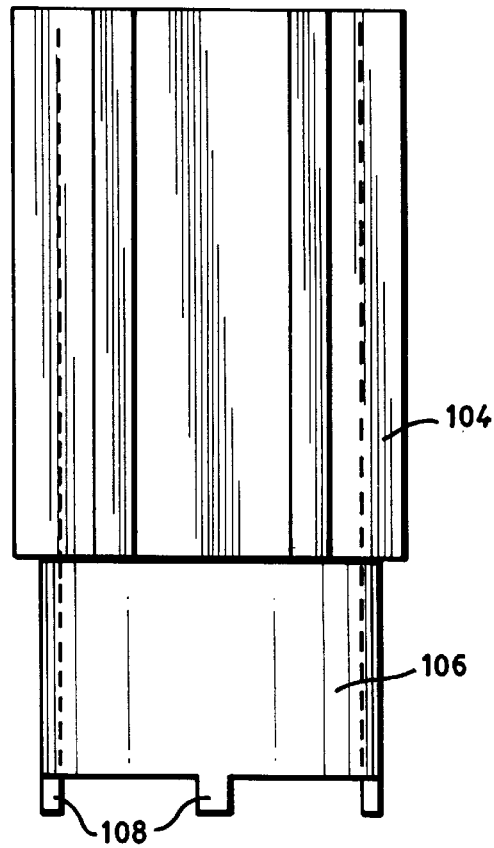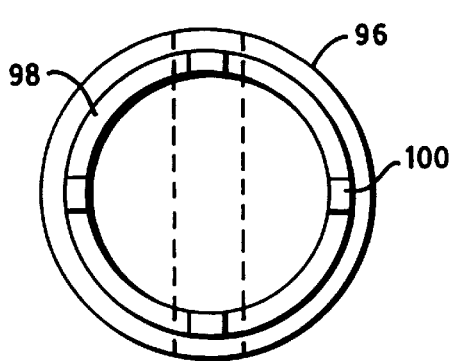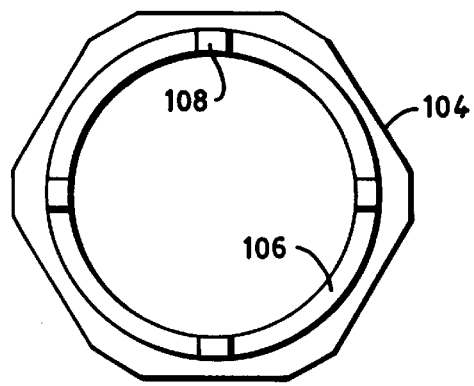
FIG. 6A  FIG. 7A
FIG. 6B  FIG. 7B

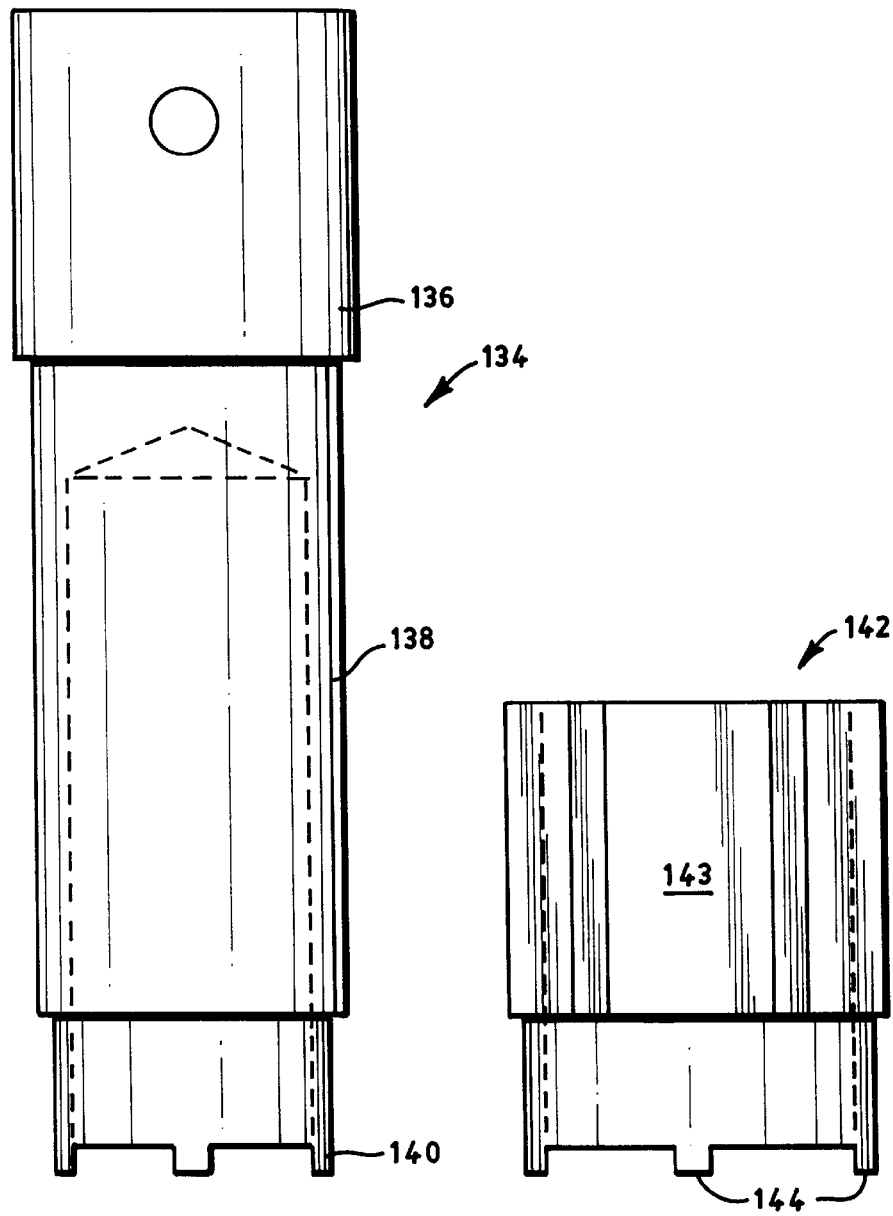
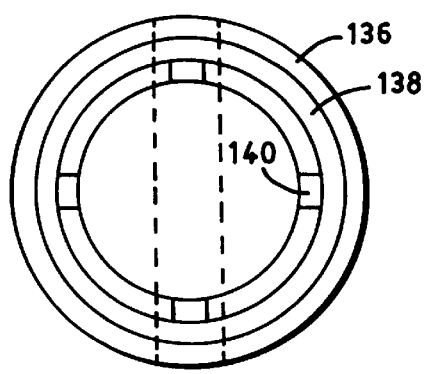
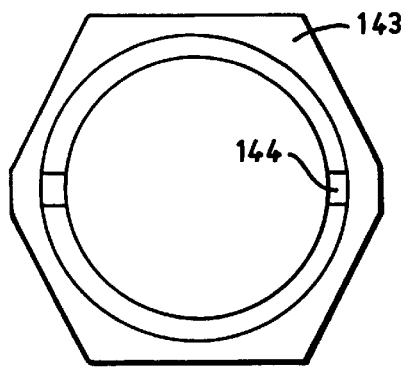

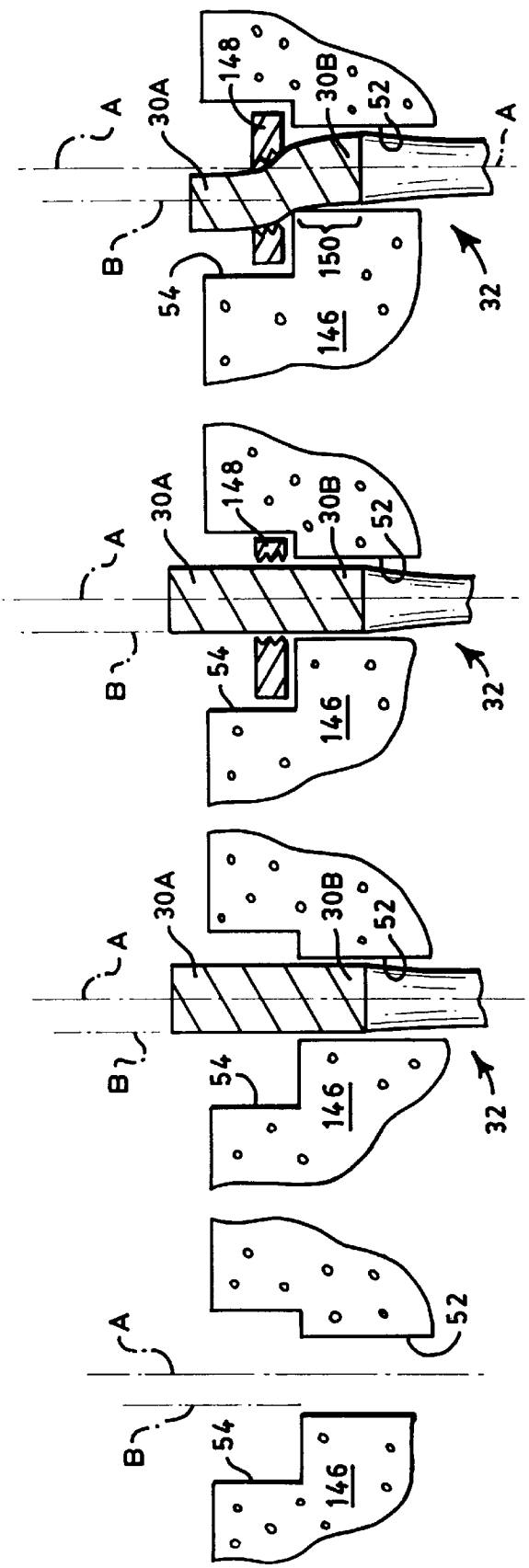

GRAFT FIXATION DEVICES

CROSS-REFERENCE TO RELATED APPLICATION

This application is a continuation-in-part of U.S. application Ser. No. 08/482,472, now U.S. Pat. No. 5,571,184, filed on Jun. 7, 1995, issued on Nov. 5, 1996 to DeSatnick.

TECHNICAL FIELD

This invention relates to fastening devices for use in bony tissue. More particularly, the invention relates to fastening devices for tensioning and fixing a bony portion of a ligament substitute or graft in a patient.

BACKGROUND OF THE INVENTION

Ligaments are elongated bands of collagenous connective tissue which interconnect bones and stabilize the movement of bones relative to one another. Each end of a ligament is affixed to a bone. Torn ligaments, particularly in the knee, ankle and shoulder, are common injuries among athletes and frequently require extensive reconstruction or replacement.

Unlike vascular tissue such as bone and skin, torn or damaged ligaments do not naturally heal because they are not vascularized, i.e., they are not supplied with a network of blood vessels which provide blood and lymph for tissue regeneration and repair. Thus, they must either be repaired, if possible, or replaced with a substitute material which will simulate the biomechanical properties of the original ligament. Surgical repair of a torn ligament, such as by mending, does not restore full strength and elasticity to the ligament and is thus of limited benefit. On the other hand, surgical replacement of a torn or damaged ligament with a natural or artificial prosthesis can substantially restore normal patient activity levels and is frequently prescribed. However, in the case of replacement with a natural or synthetic substitute, the replacement ligament must be affixed to the respective bones in a manner permitting substantially similar function to that of the original ligament.

The anterior cruciate ligament (ACL) connects the femur and the tibia within a knee joint. The ACL is the single most important stabilizing structure within the knee: it limits the movement of the bones of the joint and resists anterior displacement of the tibia with respect to the femur at all flexion positions. The ACL also resists forces which tend to hyperextend the knee.

Ruptures of the anterior cruciate ligament are among the most common injury to the knee. It is estimated that half a million ACL reconstructions are performed per year in the United States alone, with that number doubling for ACL reconstructions worldwide. Reconstruction of the ACL is a highly demanding procedure involving a determination of the correct anatomic location for an ACL substitute, the location and preparation of bony tunnel sites for the ACL substitute, and proper in situ fixation and tensioning of the ACL substitute.

One of the most widely used ACL substitutes is the bone-patellar tendon-bone (BPTB) graft. The term "graft", as used herein, refers to a natural or synthetic implantable substitute for various kinds of tissue. The central one-third of the patient's or a donor's patella tendon, along with portions of the bony insertions of the patella tendon, is used as a replacement for the damaged ACL. The bony insertions are preferably harvested as cylindrical bone plugs to facilitate implantation and fixation of the BPTB graft into osseous tunnels of the patient's knee joint. The BPTB graft is a popular choice for ACL reconstructive surgery because of its high load strength and its superior bone fixation properties.

Another commonly used ACL substitute is the iliotibial band (ITB) graft. The ITB is a section of ligament which can be harvested from a portion of a patient's or a donor's iliotibial ligament located within the anterolateral ligament structures of the knee joint.

Generally, to use such BPTB or ITB grafts, an osseous tunnel is established in both the femur and tibia of a patient, and the bone plugs of the BPTB graft, or the ends of the ITB graft, are positioned within, and affixed to, the tunnels, with a predetermined tension and angular orientation established in the tendon. In order to promote effective fusion of the bone plugs of a BPTB graft to the side walls of the osseous channels, a close fit, and preferably direct contact, is desired. It is also important, from a functional standpoint, to have a specific tension in the ligament when it is anchored in place.

Identification of the optimal location and tension of such a graft and, once identified, accomplishing the identified location and tension, are difficult tasks. Generally, the surgeon lacks adequate equipment for precisely determining the appropriate anatomic location for correct placement of the graft, for preparing the bony tunnel sites, and for anchoring and tensioning the graft, and often a limited trial-and-error approach is used.

Various devices for fixing ligaments and ligament substitutes to bone are known. For example, U.S. Pat. No. 4,537,185 to Stednitz discloses a self-drilling, self-tapping cannulated fixation screw which can be inserted over a guide wire and positioned in a desired location within a bone. Such bone screws are commonly used as graft fixation devices for the bone plugs of BPTB grafts. In such cases, a bone screw is inserted into the space between the bone plug at the graft and the wall of the osseous tunnel to establish an interference fit. Although this approach may effectively secure the bone plug in the channel ligament, the screw necessarily creates a gap on one side of the plug while driving the other side of the bone plug against the sidewall of the tunnel. This less-than-360 degree contact is less than optimal.

Other fixation devices employ various structures for coupling with a ligament or a suture and for engaging with the bone. For example, U.S. Pat. No. 5,356,435 to Thein discloses an element for fixing a ligament in a bony canal. The element includes an internal conduit for receiving an end of a ligament, and a clamping structure for securing the ligament end within the conduit. U.S. Pat. No. 5,356,413 to Martins et al. discloses a surgical anchor having a body portion and a suture-receiving bore. The body portion includes a rearward portion adapted for receiving a ligament, and a plurality of barbs extending outwardly and rearwardly from the body for engaging with the walls of a bony tunnel in a force fit.

None of these fixation devices permits a surgeon to easily fix the fibrous or bony portions of a ligament substitute in a desired position within a bony tunnel (e.g., in full 360-degree contact with the channel walls) and also establish the desired tension and angular orientation in the ligament substitute in situ. The grafted ligament substitute which is fixed with these devices may loosen under load as a result of the asymmetric positioning of the fixation device in the bony tunnel with respect to the graft and the forces on the joint. Also, torque applied to a bone screw to fix a graft may be undesirably transferred to the graft itself, thereby changing the orientation of the ligament substitute in the bony tunnel. Also, if removal of the bone screw is required, it must be either unscrewed or chipped out, leaving an unfilled hole in the bone. Also, some fixation devices are relatively large in cross-section, requiring a bony channel of relatively large diameter. Damaged or diseased host tissue may not be sufficiently strong or extensive to permit the use of large fixation devices therein.

Prior art bone graft fixation devices commonly employ a screw to fix the bone plug portion of the graft within a bony channel. Such screws typically are driven through the cancellous bone region of the bone plug. As a result, the cortical bone region of the bone plug is in abutting contact with the cancellous bone region of the bone channel. This type of contact between the bone plug and the surrounding channel may provide relatively low fixation strength between the bone plug and the channel and is therefore less desirable than cancellous-to-cancellous bone region contact.

U.S. Pat. No. 5,571,184 to DeSatnick, assigned to the assignee of the present invention and incorporated by reference into this application, discloses a graft fixation device which comprises an annular collar with two mating annular drive elements disposed concentrically therein which engage a bone graft and permit it to be selectively positioned and tensioned within a bony tunnel. Although this device overcomes some of the deficiencies of the prior art, it is not sufficiently versatile to be used in a wide variety of graft fixation applications.

It is therefore an object of the present invention to provide a graft fixation device which obviates the disadvantages of the prior art devices.

It is another object of the present invention to provide a graft fixation device which has improved graft fixation capabilities and promotes bone ingrowth between the graft and the bony channel.

It is another object of the present invention to provide a graft fixation device which can establish and maintain in situ a desired axial position and a desired axial tension for a ligament graft.

It is another object of the present invention to provide a graft fixation device by which the bone graft therein can be selectively adjusted to ensure that the cancellous bone regions of the bone channel and the bone plug portion of the graft are in contact.

Yet another object of the present invention to provide a graft fixation device which can also be used to rotate a ligament graft in situ about its longitudinal axis to achieve a desired angular orientation or create a desired spiral twist in the graft.

It is another object of the present invention to provide a graft fixation device which is minimally invasive to a patient.

SUMMARY OF THE INVENTION

The graft fixation devices of the present invention can be used to anchor and position a bone graft within a channel in a bone so that the cancellous portion of the bone graft is in contact with the cancellous portion of the channel, thus promoting rapid tissue ingrowth and accelerating graft fixation. Such graft fixators are particularly useful in reconstruction of the anterior cruciate ligament (ACL), in which a bone graft, such as a BPTB or ITB graft, is installed in bony channels drilled into the femur and tibia.

Optimum bone ingrowth and tissue integration can occur if the cancerous portion of the bone graft is in contact with the cancellous portion of the bony channel. The graft fixation devices of the present invention operate in a cam-like manner to position the graft laterally within a bony channel upon the application of a rotational force to the graft fixation device. This feature of the graft fixators of the present invention ensures that the bone graft is both securely engaged within the graft fixator and is properly positioned within the bony channel, preferably in cancellous-to-cancellous bone contact.

Accordingly, the present invention provides, in one aspect, a graft fixator for positioning and anchoring a bone graft within a bony channel. In its most general form, the graft fixator comprises a rigid cylindrical body extending about a central axis and including a bore extending therethrough substantially in the direction of the central axis. The bore extends about a second axis which is substantially parallel to, and radially offset from, the central axis.

The interior surface of the bore is adapted for receiving and engaging with a bone plug portion of a bone graft. In a preferred embodiment, the interior surface of the bore includes a plurality of annular grooves with edges that are adapted for cutting into bone. In one preferred embodiment, the annular grooves extend about the central axis, i.e., the cylinder axis, and the edges of the grooves include a bone-cutting leading edge to facilitate the initial engagement of the bone plug in the fixator.

In an alternative embodiment, the annular grooves on the interior surface of the bore extend about the second axis, i.e., the bore axis. The edges of the annular grooves in this embodiment of the graft fixator can also include a bone-cutting leading edge to facilitate engagement of the bone plug in the fixator.

The cylindrical body is adapted for receiving a rotational force applied to it about the central axis. It includes a receiving element in a first end thereof which is adapted for releasably receiving a rotatable driver. In a preferred embodiment, the receiving element comprises a plurality of slots in the first end of the cylindrical body which releasably engage with the fingers of a rotatable driver.

A method of fixing a bone graft in a bony channel generally comprises the steps of:

A. providing a bone graft from a source of viable bone graft tissue, the bone graft having a pair of generally cylindrical bone plugs joined at their proximal ends by a central tendon portion and including both cancellous and cortical bone regions;

B. preparing a channel in a bone for receiving the bone graft, wherein the channel is generally cylindrical and extends along and about a channel axis through both cortical and cancellous bone regions and includes a generally cylindrical counterbore in the bone at an end of the channel, the counterbore extending about a counterbore axis which is parallel to, and radially offset from, the channel axis;

C. providing a graft fixation device to secure a bone plug in the bony channel, the device including a rigid cylindrical body extending about a central axis and including a bore extending therethrough substantially in the direction of the central axis, the bore extending about a second axis substantially parallel to, and radially offset from, the central axis, the interior surface of the bore being adapted for engaging with a bone plug of the bone graft, the cylindrical body being adapted for receiving a rotational force applied to it about the central axis;

D. inserting the bone graft into the channel in the bone so that a proximal end of one of the bone plugs extends into the channel and a distal end of the bone plug extends into the counterbore of the channel;

E. installing the graft fixation device in a counterbore of the channel and inserting the distal end of the bone plug through the bore of the cylindrical body of the device; and F. applying a rotational force to the cylindrical body about its central axis, thereby engaging the distal end of the bone plug in the cylindrical body and effecting contact between the proximal end of the bone plug and a portion of the channel.

In a preferred embodiment, the cylindrical body is rotated by up to approximately 180 degrees to engage the bone plug and effect contact between the bone plug and the channel. Preferably, the contact is between the respective cancellous portions of the bone plug and the channel.

According to another aspect of the invention, there is provided a two-piece graft fixation device for positioning and anchoring a bone graft within a bony channel. The two-piece device comprises first and second rigid cylindrical bodies. The first rigid cylindrical body extends about a central axis and includes a first bore extending about a first axis parallel to, and radially offset from, the central axis. The second rigid cylindrical body extends about its own central axis and includes a counterbore at one end thereof. The counterbore also extends about the central axis. A second bore at an opposite end of the second cylindrical body extends about a first axis parallel to, and radially offset from, the central axis. The interior surface of the second bore includes a plurality of annular grooves with edges that are adapted for cutting into bone. The counterbore is sized to surround and slidingly engage with the first cylindrical body such that when the first cylindrical body is disposed within the counterbore of the second cylindrical body, the respective central and first axes of the first and second cylindrical bodies are in substantial alignment. A receiving element on the first cylindrical body is adapted for receiving a rotational force applied thereto about the central axis to cause lateral movement of the bone plug within and relative to the second cylindrical body and to cause a portion of the bone plug to engage with the annular grooves of the second bore. Similarly, a receiving element on the second cylindrical body is adapted for receiving a rotational force applied thereto about the central axis to cause a portion of the bone plug to contact a portion of the channel.

In a preferred embodiment, the annular grooves on the interior surface of the second bore extend about the first axis, i.e., the bore axis. In an alternate embodiment, the annular grooves extend about the central axis, i.e., the axis of the second cylindrical body.

In a preferred embodiment, the receiving elements on the first and second cylindrical bodies comprise a plurality of slots in corresponding first ends of each of the first and second cylindrical bodies for releasably receiving a rotatable driver. In addition, the receiving elements on the first cylindrical body are radially alignable with the receiving elements on the second cylindrical body to effect simultaneous driving of the two fixator parts.

A method of using the two-piece graft fixation device to fix a bone graft in a bony channel comprises the steps of:

A. providing a bone graft from a source of viable bone graft tissue, the bone graft having a pair of generally cylindrical bone plug portions joined at their proximal ends by a central tendon portion, the bone plugs including both cancellous and cortical bone regions;

B. preparing a channel in a bone for receiving the bone graft, wherein the channel is generally cylindrical and extends along and about a channel axis through both cortical and cancellous bone regions and includes a generally cylindrical counterbore in the bone at an end of the channel, the counterbore extending about a counterbore axis which is parallel to, and radially offset from, the channel axis;

C. providing a graft fixation device which includes:
  i. a first rigid cylindrical body extending about a central axis and including a first bore extending about a first axis parallel to, and radially offset from, the central axis;
  ii. a second rigid cylindrical body extending about a central axis and including a counterbore at one end thereof, the counterbore extending about the central axis, and a second bore at an opposing end thereof, the second bore extending about a first axis parallel to, and radially offset from, the central axis, the interior surface of the second bore including a plurality of annular grooves with edges adapted for cutting bone, wherein the counterbore is sized to surround and slidingly engage with the first cylindrical body such that when the first cylindrical body is disposed within the counterbore of the second cylindrical body, the respective central and first axes of the first and second cylindrical bodies are substantially aligned;
  iii. a receiving element on the first cylindrical body for receiving a rotational force applied thereto about the central axis; and
  iv. a receiving element on the second cylindrical body for receiving a rotational force applied thereto about the central axis;

D. inserting the bone graft into the channel in the bone so that a proximal end of one of the bone plugs extends into the channel and a distal end of the bone plug extends into the counterbore of the channel;

E. installing the graft fixation device in a counterbore of the channel so that the first bore of the first cylindrical body is substantially aligned with the second bore of the second cylindrical body;

F. inserting the distal end of the bone plug through the aligned first and second bores of the first and second cylindrical bodies of the fixation device;

G. applying a rotational force to the first cylindrical body relative to the second cylindrical body, thereby causing the proximal end of the bone plug to engage with the annular grooves of the second bore and causing lateral movement of the bone plug in the counterbore; and H. applying a rotational force to the second cylindrical body relative to the first cylindrical body, thereby effecting contact between the proximal end of the bone plug and a portion of the channel. Preferably, the contact is between the respective cancellous portions of the bone plug and the channel.

In a preferred embodiment, the first cylindrical body is rotated up to approximately 180 degrees to engage the bone plug in the second cylindrical body, and the second cylindrical body is rotated up to approximately 180 degrees to effect contact between the cancellous portions of the bone plug and the channel.

According to another aspect of the invention, there is provided a graft fixator kit, which comprises a graft fixator for positioning and anchoring a bone graft within a bony channel, a rotatable driver adapted for releasable engagement with the graft fixator, and a bone graft. The graft fixator is of the type described herein and generally comprises a rigid cylindrical body extending about a central axis and a bore extending therethrough substantially in the direction of the central axis. The bore extends about a second axis which is substantially parallel to, and radially offset from, the central axis. The interior surface of the bore is adapted for receiving and engaging with a bone plug portion of the bone graft. The cylindrical body is adapted for receiving a rotational force applied to it about the central axis. The bone graft includes a pair of generally cylindrical bone plugs joined at their proximal ends by a central tendon portion. The bone plugs include both cancellous and cortical bone regions.

According to still another aspect of the invention, there is provided a three-piece graft fixation device for positioning and anchoring a bone graft within a bony channel. The three-piece device comprises:

A. a rigid cylindrical shell extending about a central axis and including a bore extending through the shell substantially along and about the central axis, the wall surrounding the bore forming a circular opening in a first end of the shell and forming an elliptical opening in a second end of the shell;

B. a receiving element on the shell for receiving a rotational force applied to it about the central axis;

C. a pair of generally semicircular grip members adapted for mutual sliding engagement with one another, the grip members fitting within, and having an exterior surface adapted to slidingly engage with, the walls of the bore of the shell, each of the grip members having an interior surface adapted for gripping engagement with a bone plug installed therebetween, wherein the grip members, when not mutually engaged with one another, define an annular element having a first diameter and, when mutually engaged with one another, define an annular element having a second diameter, the first diameter being larger than the second diameter; and D. a receiving element on the grip members for receiving rotational force applied to the grip members about the central axis to engage a bone plug between the grip members.

Rotation of the shell relative to the grip members therein causes the diameter of the engaged grip members to vary between a first diameter, which is larger than the nominal diameter of the bone plug, and a second diameter, which is smaller than the first diameter and is approximately equal to the diameter of the bone plug, thereby alternately gripping and releasing a bone plug installed therebetween. Rotation of the coupled and engaged grip members rotates the bone plug within and relative to the bony channel. The engaged grip members can be rotated alone or together with the shell for coordinated movement and placement of the bone plug within the bony channel.

In a preferred embodiment, the interior surfaces of the grip members include a plurality of annular grooves with edges that are adapted for cutting bone. The edges of the annular grooves can further include a bone-cutting leading edge to facilitate the initial engagement of the bone plug in the engaged grip members.

The receiving elements on the shell and on the grip members comprise a plurality of slots in respective first ends thereof for releasably receiving a rotatable driver. In addition, the receiving elements on the grip members are radially alignable with the receiving elements on the shell to effect simultaneous driving of the shell and the engaged grip members.

A method for using the three-piece graft fixation device to fix a bone graft in a bony channel comprises the steps of:

A. providing a bone graft from a source of viable bone graft tissue, the bone graft having a pair of generally cylindrical bone plug portions joined at their proximal ends by a central tendon portion, the bone plug portions including both cortical and cancellous bone regions;

B. preparing a channel in a bone for receiving said bone graft, wherein the channel is generally cylindrical and extends along and about a channel axis through both cortical and cancellous bone regions and includes a generally cylindrical counterbore in the bone at an end of the channel, the counterbore extending about a counterbore axis which is parallel to, and radially offset from, the channel axis;

C. providing a graft fixation device including:
  i. a rigid cylindrical shell extending about a central axis and including a bore extending through the shell substantially along and about the central axis, the wall surrounding the bore forming a circular opening in a first end of the shell and forming an elliptical opening in a second end of the shell;
  ii. a receiving element on the shell for receiving a rotational force applied to the shell about its central axis;
  iii. a pair of generally semicircular grip members adapted for mutual sliding engagement with one another, the grip members fitting within, and having an exterior surface adapted to slidingly engage with, the wall of the bore of the shell, each of the grip members having an interior surface adapted for gripping engagement with a bone plug installed therebetween, wherein the grip members, when not mutually engaged with one another, define an annular element having a first diameter, and when mutually engaged with one another, define an annular element having a second diameter, the first diameter being larger than the second diameter, the first diameter being larger than the second diameter; and
  iv. a receiving element on the grip members for receiving rotational force applied thereto about the central axis;
  wherein rotation of the shell causes grip members to alternately engage and disengage, thus varying the diameter of the annular element between a first diameter, which is larger than the diameter of the bone plug, and a second diameter, which is smaller than the first diameter and substantially equal to the diameter of the bone plug, and wherein rotation of the engaged grip members effects rotation of the bone plug within and relative to the bony channel;

D. inserting the bone graft into the channel in the bone so that a proximal end of one of the bone plugs extends into the channel and a distal end of the bone plug extends into the counterbore of the channel;

E. installing the graft fixation device in a counterbore of the channel with the grip members disposed within the shell;

F. inserting the distal end of one of the bone plugs between the grip members of the device;

G. applying a sufficient rotational force to the shell about its central axis to cause the grip members to engage with one another and grip the bone plug therebetween; and H. applying a sufficient rotational force to the engaged grip members to position the bone plug within the bony channel so that the cancellous bone regions of the bone plug and the channel are in contact.

In a preferred embodiment, the shell is rotated up to approximately 180 degrees to cause the grip members to engage the bone plug therebetween. In addition, the engaged grip members are rotated up to approximately 180 degrees to position the bone plug within the bony channel so that the cancellous bone regions of the bone plug and channel are in contact.

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 1A is a plan view of a graft fixator according to one aspect of the invention;

FIG. 1B is a sectional view taken along line I—I of the graft fixator of FIG. 1A;

FIG. 2 is a side view of a bone graft including a pair of generally cylindrical bone plugs joined by a central tendon portion;

FIG. 3A is a plan view of a graft fixator according to another aspect of the invention;

FIG. 3B is a sectional view taken along line II—II of the graft fixator of FIG. 2A;

FIG. 4A is a plan view of the inner portion of a two-piece graft fixator;

FIG. 4B is a sectional view taken along line IV—IV of the inner portion of the graft fixator of FIG. 4A;

FIG. 5A is a plan view of the outer portion of the two-piece graft fixator;

FIG. 5B is a sectional view taken along line V—V of the outer portion of the graft fixator of FIG. 5A;

FIG. 6A is a side view of a driver for the inner portion of the two-piece graft fixator;

FIG. 6B is an end view of the driver of FIG. 6A;

FIG. 7A is a side view of a driver for the outer portion of the two-piece graft fixator;

FIG. 7B is an end view of the driver of FIG. 7A;

FIG. 12A is a side view of a driver for the grip members of the three-piece graft fixator of FIGS. 8–11;

FIG. 12B is an end view of the driver of FIG. 12A;

FIG. 13A is a side view of a driver for the shell of the three-piece graft fixator of FIGS. 8–11;

FIG. 13B is an end view of the driver of FIG. 13A;

FIGS. 16A–16D are simplified sectional views of the steps in a method of fixing a bone graft within a bony channel.

DETAILED DESCRIPTION OF THE PREFERRED EMBODIMENT

Figure 8A:
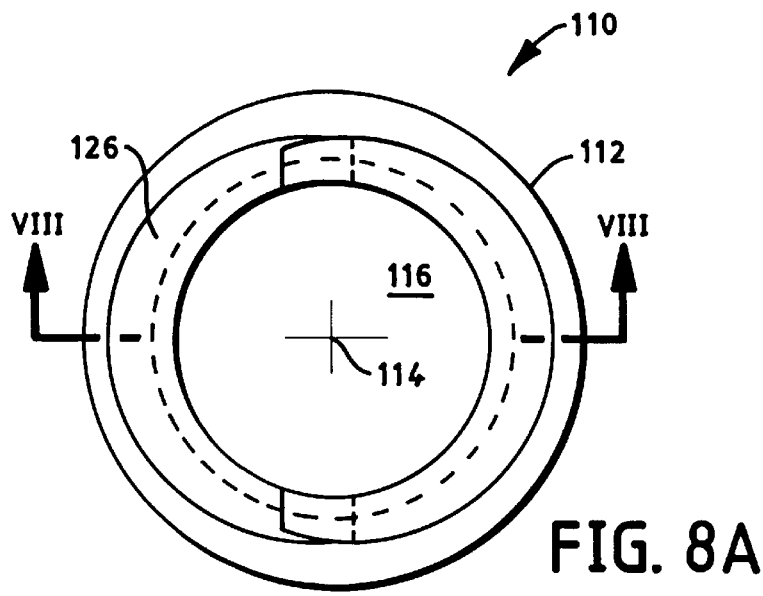
FIG. 8A is a plan view of a three-piece graft fixator in which the grip members are coupled within the shell but not mutually engaged with one another.
Figure 8B:
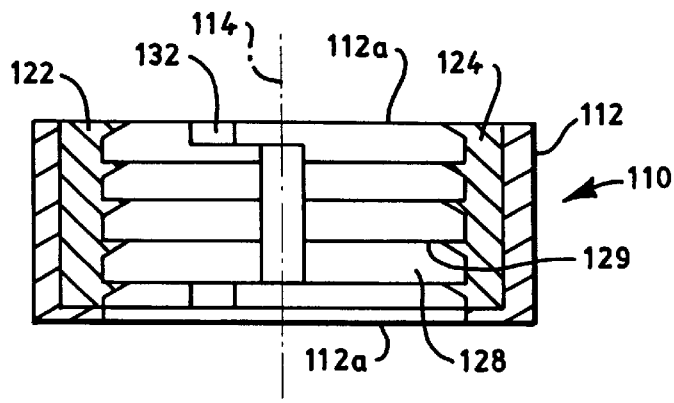
FIG. 8B is a sectional view taken along line VIII—VIII of the graft fixator of FIG. 8A.

A graft fixation device according to one aspect of the invention is illustrated in FIGS. 1A–1B. This graft fixator 20 comprises a rigid cylindrical body 22 which extends about a central axis 24. The body 22 includes a bore 26 which extends substantially in the direction of the central axis 24. The bore 26 extends about a second axis 28 which is substantially parallel to, and radially offset from, the central axis 24. The bore is thus eccentric with respect to the outer diameter of the cylindrical body, as indicated by eccentricity E in FIG. 1A.

The interior surface of the bore 26 is adapted for receiving and engaging with a bone plug portion 30 of a bone graft 32, illustrated in FIG. 2. The bone graft 32 includes a pair of generally cylindrical bone plugs 30 which are joined at their proximal ends by a central tendon portion 34. The bone plugs 30 preferably include both cortical bone regions 36 and cancellous bone regions 38. A bone plug portion of the bone graft may be, for example, on the order of about 25 mm in length, and the central tendon portion may be approximately twice that length, although other dimensions are also feasible, depending on the location for the graft and other factors.

In a preferred embodiment, the interior surface of the bore 26 includes a plurality of annular grooves 39, as shown in FIG. 1B. The annular grooves include edges 41 that are adapted for cutting bone, and particularly for cutting into the cortical and cancellous bone regions 36, 38 of the bone plug portions 30 of the bone graft as the cylindrical body 22 is rotated about the bone plugs in the bony channel, as detailed more fully below.

The edges 41 of the annular grooves in the interior surface of the bore 26 can include a relatively sharp bone-cutting leading edge 50, as shown in FIG. 3A. This bone-cutting leading edge is designed to initiate a cut into the cortical and/or cancellous regions 36, 38 of the bone plug and facilitates the initial engagement of the edges of the grooved interior surface of the bore with the bone plug 30.

In one preferred embodiment, the annular grooves 39 are concentric with the bore, or second, axis 28, as illustrated in FIG. 1A. The bore is thus grooved to a uniform annular depth. It can be seen that rotation of a bone plug 32 within the bore 26 of the graft fixator of FIGS. 1A–1B causes the bone plug to be uniformly cut into by the edges 41. In addition, rotation of the graft fixator of FIGS. 1A–1B about its central axis 24 causes the bore 26, which is eccentric relative to the central axis 24, to rotate about the central axis 24. This lateral movement of the bore, and in particular a bone plug installed therein, enables the bone plug to be placed in abutting contact with a portion of the bony channel wall, as detailed more fully below.

In an alternate embodiment, the annular grooves 39 are concentric with the central, or cylinder, axis 24, as illustrated in FIGS. 3A–3B. As shown most clearly in FIG. 3B, the annular grooves are at a maximum depth at one side of the cylindrical body and are at a minimum depth at an opposite side of the body.

The cylindrical body 22 further includes a receiving element 40 at a first end thereof in the form of, for example, a plurality of slots 42 which are adapted to receive a rotational force applied to the cylindrical body about its central axis 24 by a rotatable driver 44. Other forms of a receiving element which are adapted for receiving an applied rotational force are considered to be within the scope of the invention.

The rotatable driver generally includes a handle 46 adapted for manual or remote manipulation, and a plurality of fingers 48 which releasably couple with the slots 42 in the cylindrical body 22 of the fixator. Typical rotatable drivers are illustrated in FIGS. 6, 7, 12 and 13.

A two-piece graft fixator 60 which operates in a similar manner to the single-piece graft fixator is illustrated in FIGS. 4A–4B and 5A–5B. The fixator comprises a first rigid cylindrical body 62, illustrated in FIGS. 4A–4B, extending about a central axis 64. The first cylindrical body 62 includes a bore 66 which extends about a first axis 68 that is parallel to, and radially offset from, the central axis 64. The bore 66 is thus eccentric relative to the central axis 64 of the cylindrical body.

A second rigid cylindrical body 70, illustrated in FIGS. 5A–5B, also extends about a central axis 72 and includes a counterbore 74 at one end and a second bore 76 at an opposite end, as shown most clearly in FIG. 5B. The counterbore 74 extends about the central axis 72 of the cylindrical body, whereas the second bore 76 extends about a first axis 78 which is parallel to, and radially offset from, the central axis 72, as shown in FIG. 5A.

The interior surface of the second bore 76 of the second cylindrical body 70 includes a plurality of annular grooves 80 which have edges 81 that are adapted for cutting bone. The counterbore 74 of the second cylindrical body is sized to surround and slidingly engage with the first cylindrical body 62, such that when the first body 62 is disposed within the counterbore 74 of the second body 70, the central axis 64 of the first body is substantially aligned with the central axis 72 of the second body, and the first axis 68 of the first bore 66 of the first body is substantially aligned with the first axis 78 of the second bore 76 of the second body.

The first cylindrical body 62 further includes receiving elements 82 in a first end thereof in the form of, for example, a plurality of slots 84 which are adapted to receive a rotational force applied to the first cylindrical body about the central axis 64. The second cylindrical body 70 also includes receiving elements 86 in a first end thereof in the form of, for example, a plurality of slots 88 which are adapted to receive a rotational force applied to the second cylindrical body 70 about central axis 72. The first cylindrical body 62 has a smooth, i.e., ungrooved, external surface 90 which permits sliding engagement of the first cylindrical body within the counterbore of the second cylindrical body, which has a corresponding smooth, i.e., ungrooved, interior surface 92.

As shown in FIG. 5A–5B, the annular grooves 80 of the second cylindrical body 70 preferably extend about the bore, or first, axis 78 so that the grooving is uniformly deep and a bone plug within the bore is contacted to a uniform depth all around by bone-cutting edges. In an alternate embodiment, the grooves extend about the central axis of the second cylindrical body.

A first rotatable driver 94 for the first cylindrical body is illustrated in FIGS. 6A–6B. The driver is generally cylindrical and includes a handle 96 adapted for manual or remote manipulation. The driving end 98 of the driver is tubular and terminates in a plurality of fingers 100 which releasably engage with the slots 84 in the first cylindrical body to impart rotational force thereto.

A second rotatable driver 102 for the second cylindrical body is illustrated in FIGS. 7A–7B. The driver is tubular with a faceted or textured handle 104 which facilitates gripping of the driver. The driving end 106 of the driver is tubular and generally cylindrical. It terminates in a plurality of fingers 108 which releasably engage with the slots 88 in the second cylindrical body to impart rotational force thereto.

The second rotatable driver 102 preferably has an inner diameter which is sufficiently large to accommodate the first rotatable driver 94 axially inside it, so that the two drivers can be telescopically arranged. By securing the two drivers together in this arrangement, the first and second cylindrical bodies can be rotated together if desired. Such an arrangement is useful for simultaneous rotation and lateral positioning of the bone plug in the channel.

The rotatable drivers 94, 102 for the respective first and second cylindrical bodies of the two-piece graft fixator can be telescoped as previously described to coordinate the application of rotational force to the respective bodies. In particular, application of rotational force to the second cylindrical body may include simultaneous application of rotational force to the first cylindrical body to ensure that the first and second bores of the respective bodies remain aligned during rotation of the device and lateral positioning of the bone plug within the channel. This feature prevents the introduction of strain or torque into the bone plug after it is gripped by the bone-cutting edges of the second cylindrical body.

A three-part graft fixator 110 according to another aspect of the present invention is illustrated in FIGS. 8–11. This fixator comprises a rigid cylindrical shell 112 which extends about a central axis 114. The shell includes a bore 116 which extends through the shell substantially along and about the central axis 114. As shown most clearly in FIGS. 8B and 11A–B, the wall 117 surrounding the bore 116 forms a circular opening in a first end 112a of the shell and an elliptical opening in a second end 112b of the shell. As shown in FIG. 11A, the shell includes a receiving element 118 in the second end 112b in the form of, for example, a plurality of slots 120 adapted for receiving a rotational force applied to the shell about the central axis 114.

Figure 8C:
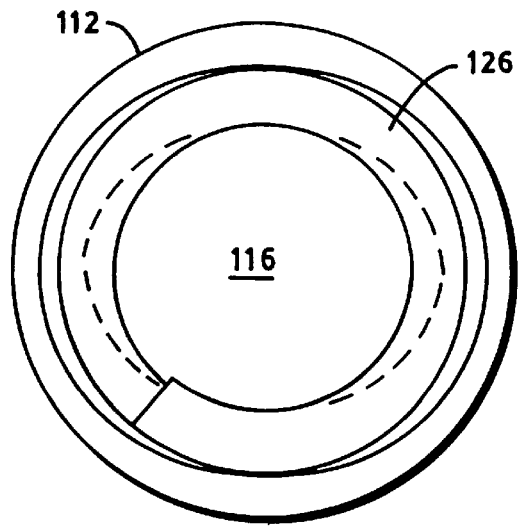
FIG. 8C is a plan view of the three-piece graft fixator of FIG. 8A, in which the grip members are coupled within the shell and mutually engaged with one another.
Figure 9A:
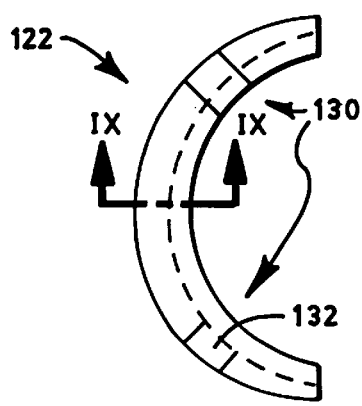
FIG. 9A is a plan view of one of the grip members of the three-piece graft fixator of FIG. 8A.
Figure 10A:
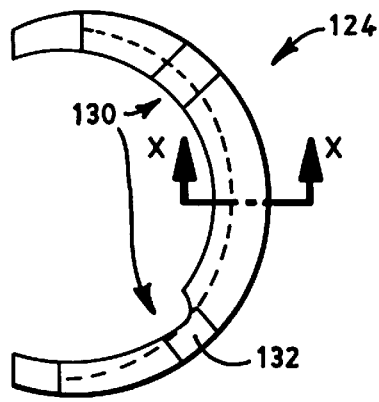
FIG. 10A is a plan view of the other grip member of the three-piece graft fixator of FIG. 8A.
Figure 9B:
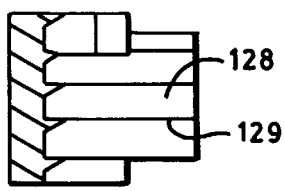
FIG. 9B is a sectional view taken along line IX—IX of the grip member of FIG. 9A.
Figure 10B:
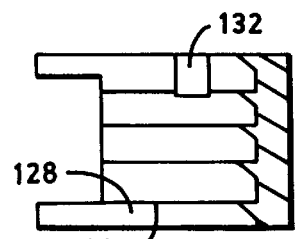
FIG. 10B is a sectional view taken along line X—X of the grip member of FIG. 10A.
Figure 11A:
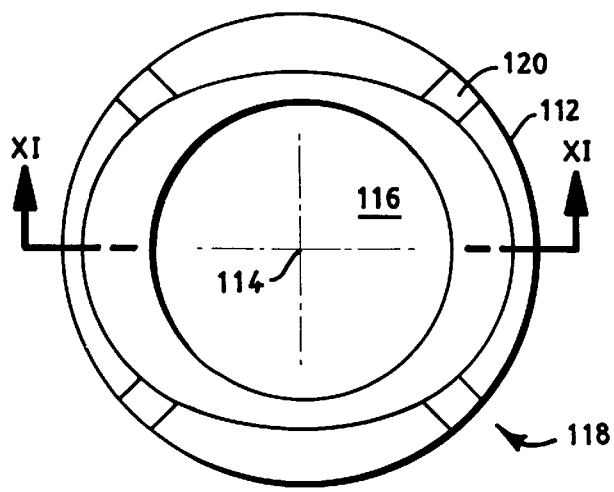
FIG. 11A is a plan view of the outer shell portion of the three-piece graft fixator of FIG. 8A.
Figure 11B:
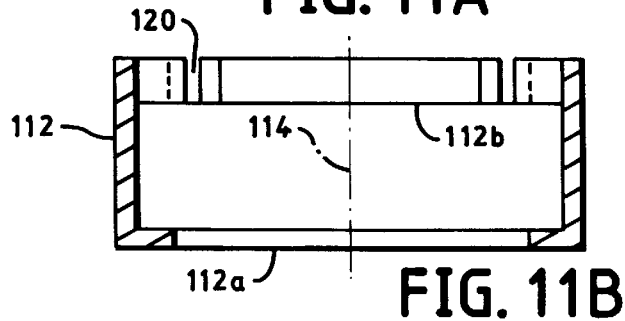
FIG. 11B is a sectional view taken along line XI—XI of the outer shell portion of FIG. 11A.

The three-part fixator additionally includes a pair of generally semicircular rigid grip members 122, 124, as shown in FIGS. 9–10. The grip members are adapted for mutual sliding engagement with one another, shown most clearly in FIGS. 8A and 8C. The grip members fit within and slidingly engage with the wall 117 of the bore 116 of the cylindrical shell 112.

When coupled together, the grip members 122, 124 define an annular element 126 which has a diameter which varies between two sizes, as illustrated in FIGS. 8A and 8C. When the grip members are coupled, yet not mutually engaged with one another, as shown in FIG. 8A, the annular element 126 has a first diameter which is larger than the nominal diameter of the bone plug to be installed therebetween. When the grip members are coupled and mutually engaged with one another, as detailed below and as shown in FIG. 8C, the annular element 126 has a second diameter which is smaller than the first diameter and which is substantially equal to, and preferably sized for interfering engagement with, the diameter of the bone plug.

Each of the grip members 122, 124 has an interior surface which is adapted for gripping engagement with a bone plug installed between them. In a preferred embodiment, the interior surface of the grip members 122, 124 includes a plurality of annular grooves 128 with edges 129 adapted for cutting bone. The annular grooves and cutting edges can include a bone-cutting leading edge to facilitate the initiation of a cut into the bone as the bone plug is installed and secured within the grip members.

The grip members additionally include a receiving element 130 in respective first ends thereof in the form of, for example, a plurality of slots 132 which are adapted to receive a rotational force applied to the annular element about the central axis 114.

Application of rotational force to the cylindrical shell 112 relative to the coupled grip members 122, 124 therein causes the grip members to alternately engage and disengage in a cam-like manner as the elliptical portion of the shell 112 slides over and around the exterior surfaces of the grip members, thus causing the diameter of the annular element 126 formed from the engagement of the grip members to vary between the first larger diameter and the second smaller diameter. When a bone plug 30 is installed between the grip members, this rotation of the shell around and relative to the grip members causes the grip members alternately to grip and release the bone plug between them. When the grip members are mutually engaged with one another and with a bone plug therebetween, the annular element thus formed is at its smaller diameter. It can then be rotated by application of rotational force thereto via slots 132. Such rotation of the annular element 126 causes the bone plug secured therein to rotate together with the annular element and relative to the cylindrical shell 112 and to the bony channel within which the fixator is installed, thereby positioning the bone plug desirably within the channel so that the cancellous bone regions of the bone plug and channel are in contact.

A set of rotatable drivers 134, 142 for the inner and outer portions of the three-piece fixator is illustrated in FIGS. 12–13. The inner driver 134 includes a handle 136 adapted for manual or remote manipulation and a generally tubular drive end 138 which terminates in a plurality of fingers 140 which are adapted for releasable engagement with the slots 132 in the annular element 126. An outer driver 142 includes a generally tubular handle 143 and a plurality of fingers 144 which are adapted for releasable engagement with the slots 120 in the cylindrical shell 112. The inner and outer drivers can be telescoped, as previously described in connection with other fixator drivers, for coordinated rotation of both the shell 112 and the annular element 126.

Figure 14:
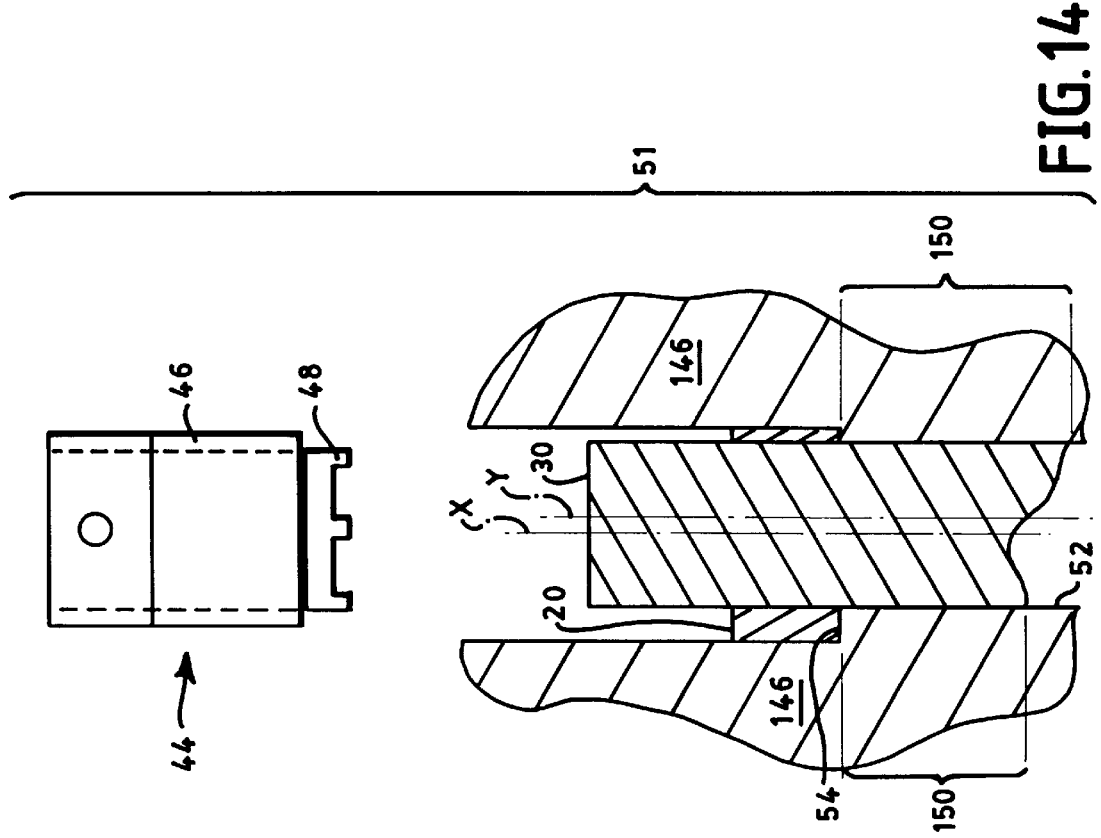
FIG. 14 is a simplified sectional view of a graft fixator kit which includes a graft fixator, a driver, and a bone plug, shown installed a bony channel (in phantom)

A graft fixator kit 51 which incorporates the graft fixators of the present invention is illustrated generally in FIG. 14. The kit includes at least one graft fixator 20 of the type described herein, a rotatable driver 44 of the type described herein, and a bone graft 32 of the type described herein. The bone graft 32 is fixed within a bony channel 52 extending about a channel axis Y in a bone 146, shown in phantom in FIG. 14. The graft fixator 20 is disposed within the channel 52 in a counterbore 54 which extends about a counterbore axis X which is eccentric with respect to the channel axis Y. Rotation of the graft fixator 20 within the counterbore 54 by application of rotational force on the fixator with the driver 44 engages the bone plug 30 in the fixator and causes the bone plug to move both laterally within the channel, as a result of the eccentricity of the bore in the fixator. This lateral movement positions the bone plug in abutting contact with a portion of the channel wall, designated at region 150, thus promoting rapid tissue ingrowth and graft fixation. Preferably, the fixator and bone plug therein are rotated to a sufficient degree to ensure that maximum contact is made between the cancellous bone regions of the bone plug and the channel.

Figure 15:
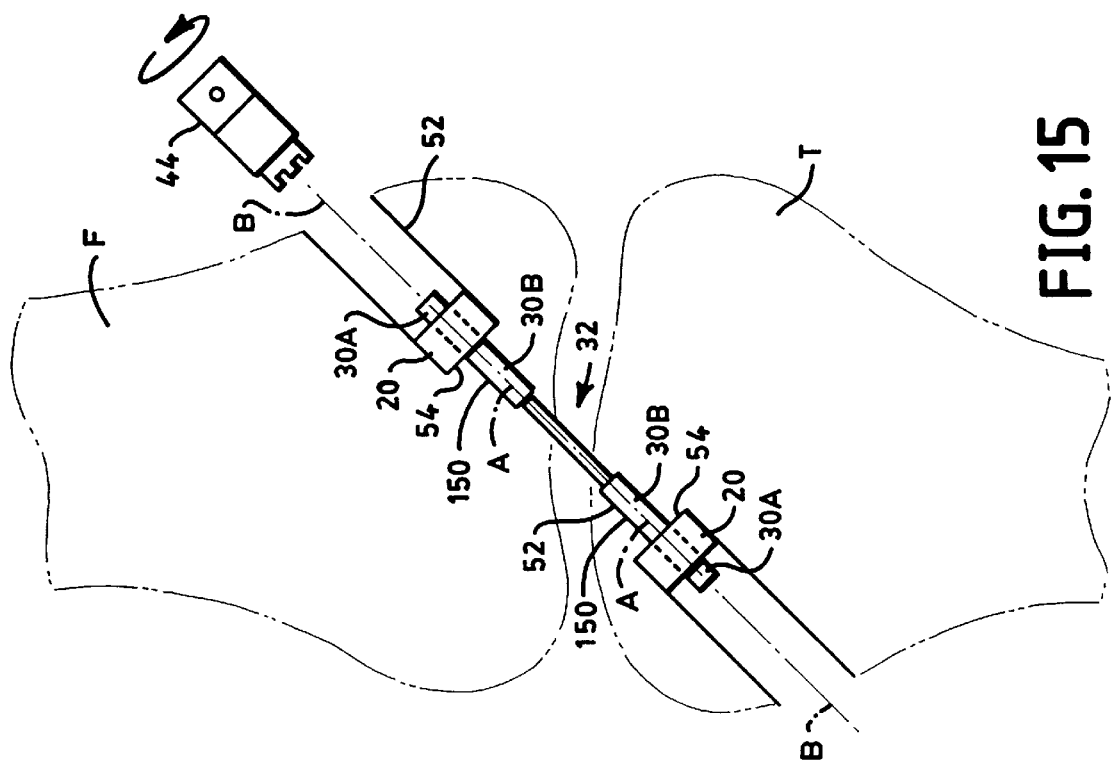
FIG. 15 is a side view of a graft fixator as installed in a bony channel (in phantom) according to a method of the invention.

FIG. 15 illustrates a general method of fixing a bone graft 32 in a bony channel 54. First, a suitable bone graft 32 is harvested from a source of viable bone graft tissue, such as the patella tendon. One or more bony channels 52 are prepared in the bones of the graft recipient, such as by drilling intersecting holes into the recipient's femur F and tibia T. The channel 52 is generally cylindrical and extends along a central channel axis A. The channel 52 terminates at each end in a counterbore 54 which extends about a counterbore axis B, which is parallel to and radially offset from the central channel axis A. A graft fixation device 20 as previously described is provided for the bone plug 30 to be anchored within the channel. The bone graft 32 is inserted into the bony channel 52 so that a proximal end 30B of one of the bone plugs 30 extends into the channel and a distal end 30A of the bone plug extends into the counterbored portion of the channel, as shown in FIGS. 14 and 15. The graft fixation device 20 is then installed in the counterbored portion of the channel around the distal end 30A of the bone plug 30. A rotational force is applied to the fixation device about its central axis with a rotatable driver 44. Upon application of such force, the distal end 30A of the bone plug is cut into and gripped by the leading and annular bone-cutting edges of the fixation device. In addition, rotation of the bone plug 30 in the device causes the bone plug to move laterally within and relative to the bony channel 52, thus bringing the proximal portion 30B of the bone plug into abutting contact with a portion of the wall of the bony channel, shown at region 150 in FIG. 14.

Because the exterior profile of the graft fixator is generally cylindrical, it fits and rotates smoothly within any substantially circular hole, such as, for example, the counterbored portion of the bony channel. However, because the bore of the fixator is generally eccentric with respect to the central axis of rotation of the cylindrical body within which the bore is disposed, rotation of the fixator causes the bore, and a bone plug secured therein, to move laterally within and relative to a bony channel, thus enabling the bone plug to be positioned in close abutting contact with a portion of the wall of the channel, as indicated generally at region 150. It is possible to effect sufficient engagement of the bone plug in the cylindrical body, and sufficient contact between the bone plug and a portion of the channel wall to promote satisfactory tissue ingrowth and graft integration, by rotating the fixator within the bony channel by up to about 180 degrees, or one-half turn of the rotatable driver and fixator.

The general method of fixation of a bone graft within a bony channel for the fixators according to the present invention and described herein is illustrated stepwise in FIGS. 16A–16D. FIG. 16A shows a bony channel 52 drilled into a bone 146. The channel 52 extends generally along a channel axis A and terminates in a generally cylindrical counterbore 54 extending about a separate counterbore axis B which is substantially parallel to, and radially offset from, the channel axis A. The counterbore 54 is thus eccentric with respect to the channel axis A.

FIG. 16B shows the bony channel and the counterbore in the bone with a bone graft 32 installed in the channel. The bone graft includes a central tendon portion 34 joining a pair of bone plugs 30. The distal end 30A of the bone plug 30 extends beyond the end of the channel into the counterbore 54, whereas the proximal end 30B of the bone plug extends into the channel.

FIG. 16C shows the bone graft installed in the channel with a graft fixator 148 according to the invention installed around a portion of the distal end 30A of the bone plug. The graft fixator comprises a rigid, generally cylindrical body extending about a first axis and having a bore extending therethrough about a second axis which is substantially parallel to, and radially offset from, the first axis, as described previously in connection with various embodiments of the invention. The bore in the fixator is thus radially offset from, or eccentric relative to, the central axis of the fixator.

FIG. 16D illustrates the result of application of a rotational force to the fixator with a bone plug installed therein. Rotation of the fixator by up to 180 degrees engages the bone plug within the eccentric bore of the fixator and rotates it about the central axis of the fixator, resulting in lateral movement of the bore and the bone plug secured therein. Substantial force is applied to the bone plug 30 to move it laterally within the bone channel 52 and create a zone 150 of abutting contact between the cancellous bone regions of the bone plug and channel. This bone-to-bone contact area promotes ingrowth of new bone cells into the interface region between the bone plug and the channel wall, thus enhancing tissue integration and graft fixation strength.

The fixators of the present invention are superior to those known in the prior art, as a they can be selectively positioned both rotationally and laterally within a bone channel. The bone plug portions of the graft can be rotated and moved laterally to ensure maximum contact between the cancellous bone regions of the bone plugs and the bone channel. Similarly, the central tendon portion of the bone graft can be rotated and positioned as desired, and the tension thereon can be adjusted, by application of rotational force on the graft fixators at each end thereof.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

We claim:

1. A graft fixator for positioning and anchoring a bone graft within a bony channel, comprising:

A. a rigid cylindrical body extending about a central axis and including a bore extending therethrough substantially in the direction of said central axis, said bore extending about a second axis substantially parallel to, and radially offset from, said central axis, the interior surface of said bore being adapted for receiving and engaging with a bone plug portion of a bone graft; and B. means on said cylindrical body for receiving a rotational force applied to said cylindrical body about said central axis, wherein the interior surface of said bore includes a plurality of annular grooves with edges adapted for cutting bone, wherein the annular grooves of said interior surface of said bore extend about said second axis, wherein said edges of said annular grooves include-a bone-cutting leading edge to facilitate engagement of said bone plug in said fixator.

* * * * *